(12) United States Patent
Denison et al.

(10) Patent No.: US 9,327,117 B2
(45) Date of Patent: May 3, 2016

(54) BLADDER SENSING USING IMPEDANCE AND POSTURE

(75) Inventors: Timothy J. Denison, Minneapolis, MN (US); Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 184 days.

(21) Appl. No.: 13/264,023

(22) PCT Filed: Apr. 20, 2010

(86) PCT No.: PCT/US2010/031760
§ 371 (c)(1),
(2), (4) Date: Oct. 12, 2011

(87) PCT Pub. No.: WO2010/123907
PCT Pub. Date: Oct. 28, 2010

(65) Prior Publication Data
US 2012/0035496 A1 Feb. 9, 2012

Related U.S. Application Data

(60) Provisional application No. 61/172,614, filed on Apr. 24, 2009.

(51) Int. Cl.
| | | |
|---|---|---|
| A61B 5/04 | (2006.01) | |
| A61B 5/05 | (2006.01) | |
| A61B 5/00 | (2006.01) | |
| A61N 1/36 | (2006.01) | |
| A61B 5/053 | (2006.01) | |
| A61B 5/11 | (2006.01) | |
| A61B 5/20 | (2006.01) | |

(52) U.S. Cl.
CPC ............ *A61N 1/36007* (2013.01); *A61B 5/053* (2013.01); *A61B 5/1116* (2013.01); *A61B 5/204* (2013.01); *A61B 5/6883* (2013.01); *A61B 5/7203* (2013.01); *A61B 5/686* (2013.01); *A61B 2560/0462* (2013.01); *A61B 2562/0219* (2013.01)

(58) Field of Classification Search
CPC ....................................................... A61B 5/00
USPC ......................... 600/546, 547, 573, 574, 579
See application file for complete search history.

(56) References Cited

U.S. PATENT DOCUMENTS

| | | | | |
|---|---|---|---|---|
| 4,901,725 A | * | 2/1990 | Nappholz et al. ............... | 607/17 |
| 5,103,835 A | * | 4/1992 | Yamada et al. ............... | 600/547 |
| 5,409,011 A | * | 4/1995 | Alexeev et al. ............... | 600/547 |
| 5,807,278 A | * | 9/1998 | McRae ......................... | 600/579 |
| 5,876,425 A | * | 3/1999 | Gord et al. ....................... | 607/56 |
| 5,957,958 A | * | 9/1999 | Schulman et al. .............. | 607/56 |
| 6,002,957 A | * | 12/1999 | Finneran ....................... | 600/382 |
| 6,104,949 A | * | 8/2000 | Pitts Crick et al. ........... | 600/547 |
| 6,238,423 B1 | * | 5/2001 | Bardy ............................. | 607/40 |
| 6,360,123 B1 | * | 3/2002 | Kimchi et al. ................ | 600/547 |

(Continued)

OTHER PUBLICATIONS

Walter, J.S., et al., J Spinal Cord Med. Apr. 1995;18(2):98-102.

*Primary Examiner* — Rene Towa
*Assistant Examiner* — May Abouelela
(74) *Attorney, Agent, or Firm* — Shumaker & Sieffert, P.A.

(57) ABSTRACT

This disclosure provides techniques for bladder sensing. In accordance with the techniques described in this disclosure, a device may measure the impedance of a bladder, determine the posture of a patient, and determine a status of the bladder based on the impedance and posture.

34 Claims, 9 Drawing Sheets

(56) References Cited

U.S. PATENT DOCUMENTS

| | | | |
|---|---|---|---|
| 6,393,323 B1* | 5/2002 | Sawan et al. | 607/41 |
| 6,570,053 B2* | 5/2003 | Roe et al. | 604/361 |
| 6,658,297 B2* | 12/2003 | Loeb | 607/40 |
| 6,659,936 B1* | 12/2003 | Furness et al. | 600/30 |
| 6,834,436 B2 | 12/2004 | Townsend et al. | |
| 7,276,057 B2* | 10/2007 | Gerber | 604/891.1 |
| 7,415,308 B2* | 8/2008 | Gerber et al. | 607/41 |
| 7,474,911 B2* | 1/2009 | Ya'akov et al. | 600/407 |
| 7,502,649 B2* | 3/2009 | Ben-Haim et al. | 607/40 |
| 7,519,429 B2* | 4/2009 | Sawan et al. | 607/60 |
| 7,522,061 B2* | 4/2009 | Rondoni et al. | 340/573.5 |
| 7,613,516 B2* | 11/2009 | Cohen et al. | 607/41 |
| 7,769,460 B2* | 8/2010 | Gerber | 607/41 |
| 7,855,653 B2* | 12/2010 | Rondoni et al. | 340/573.5 |
| 8,426,669 B2* | 4/2013 | Zhou et al. | 604/361 |
| 8,546,638 B2* | 10/2013 | Zhou et al. | 604/361 |
| 2002/0022786 A1* | 2/2002 | Takehara et al. | 600/547 |
| 2002/0022787 A1* | 2/2002 | Takehara et al. | 600/547 |
| 2005/0070969 A1* | 3/2005 | Gerber | 607/40 |
| 2005/0113878 A1* | 5/2005 | Gerber | 607/39 |
| 2006/0122659 A9* | 6/2006 | Gerber | 607/39 |
| 2006/0190051 A1* | 8/2006 | Gerber et al. | 607/41 |
| 2006/0211951 A1* | 9/2006 | Milijasevic et al. | 600/547 |
| 2006/0264775 A1* | 11/2006 | Mills et al. | 600/547 |
| 2007/0027494 A1* | 2/2007 | Gerber | 607/41 |
| 2007/0100387 A1 | 5/2007 | Gerber | |
| 2007/0225616 A1* | 9/2007 | Brown et al. | 600/587 |
| 2007/0252713 A1* | 11/2007 | Rondoni et al. | 340/573.5 |
| 2007/0252714 A1* | 11/2007 | Rondoni et al. | 340/573.5 |
| 2007/0255176 A1* | 11/2007 | Rondoni et al. | 600/573 |
| 2008/0039738 A1* | 2/2008 | Dinsmoor et al. | 600/547 |
| 2008/0079444 A1* | 4/2008 | Denison | 324/679 |
| 2008/0081958 A1* | 4/2008 | Denison et al. | 600/300 |
| 2008/0103414 A1* | 5/2008 | Song | 600/573 |
| 2008/0221468 A1* | 9/2008 | Stahmann et al. | 600/529 |
| 2008/0262376 A1* | 10/2008 | Price | 600/547 |
| 2008/0300650 A1 | 12/2008 | Gerber et al. | |
| 2009/0048538 A1 | 2/2009 | Levine et al. | |
| 2010/0137736 A1* | 6/2010 | Addington et al. | 600/546 |
| 2010/0217148 A1* | 8/2010 | Binder | 600/547 |
| 2011/0060239 A1* | 3/2011 | Gaw | 600/547 |
| 2012/0109008 A1* | 5/2012 | Charlez et al. | 600/573 |

* cited by examiner

BLADDER SENSING USING IMPEDANCE AND POSTURE

TECHNICAL FIELD

The disclosure relates to implantable medical devices and, more particularly, devices for the treatment of urinary incontinence.

BACKGROUND

Urinary incontinence, or an inability to control urinary function, is a common problem afflicting people of all ages, genders, and races. Various muscles, nerves, organs and conduits within the pelvic floor cooperate to collect, store and release urine. A variety of disorders may compromise urinary tract performance, and contribute to incontinence. Many of the disorders may be associated with aging, injury or illness.

In some cases, urinary incontinence can be attributed to improper sphincter function, either in the internal urinary sphincter or external urinary sphincter. For example, aging can often result in weakened sphincter muscles, which causes incontinence. Some patients may also suffer from nerve disorders that prevent proper triggering and operation of the bladder or sphincter muscles. Nerves running though the pelvic floor stimulate contractility in the sphincter. A breakdown in communication between the nervous system and the urinary sphincter can result in urinary incontinence. As used in this disclosure, the term "urinary incontinence" includes disorders in which urination occurs when not desired, such as stress or urge incontinence, and disorders in which urination does not occur as desired, such as urinary retention disorder.

Therapies for treating urinary incontinence include delivery of electrical stimulation. For example, delivery of electrical stimulation from an implantable medical device to nerves in the pelvic floor, such as the sacral nerve, and pudendal nerve and its branches, and dorsal genital nerve may provide an effective therapy for urinary incontinence. Electrical stimulation of the sacral nerve may induce sphincter constriction and thereby close or maintain closure of the urethra at the bladder neck. In addition, electrical stimulation of the bladder wall may enhance pelvic floor muscle tone and assist fluid retention in the bladder or voiding fluid from the bladder.

SUMMARY

In general, this disclosure provides techniques for bladder sensing. In accordance with the techniques described in this disclosure, an implantable medical device may measure the electrical impedance of tissue associated with at least a portion of a bladder, determine the posture of a patient, and determine a status of the bladder based on the impedance and posture. Bladder impedance may vary as a function of the volume of the fluid in the bladder and the posture of the patient. For example, the impedance of a half-full bladder may vary depending on whether the patient is seated or standing. By measuring the impedance of a patient's bladder containing a known volume of fluid as the patient is positioned in various postures, and programming the measurements associated with the postures into a memory, an implantable medical device may provide accurate information as to the filling status of a patient's bladder.

In one example, the disclosure provides a system for determining a status of a urinary bladder of a patient. The system comprises an impedance measurement unit that measures an impedance of the bladder, a posture sensor that determines a posture of the patient; and a processor that determines a status of the bladder based on the impedance and the posture.

In some examples, the disclosure provides a method for detecting a status of a urinary bladder of a patient using an implanted device. The method comprises measuring an impedance of the bladder with the implanted device, determining a posture of the patient, and determining a status of the bladder based on the impedance and the posture.

In another example, the disclosure provides a device for determining a status of a urinary bladder of a patient. The device comprises an impedance measurement unit that measures an impedance of the bladder, a posture sensor that determines a posture of the patient, and a processor that determines a status of the bladder based on the impedance and the posture.

In another example, the disclosure provides a device for detecting a status of a urinary bladder of a patient using an implanted device. The device comprises means for measuring an impedance of the bladder with the implanted device, means for determining a posture of the patient, and means for determining a status of the bladder based on the impedance and the posture.

DETAILED DESCRIPTION

Figure 1:
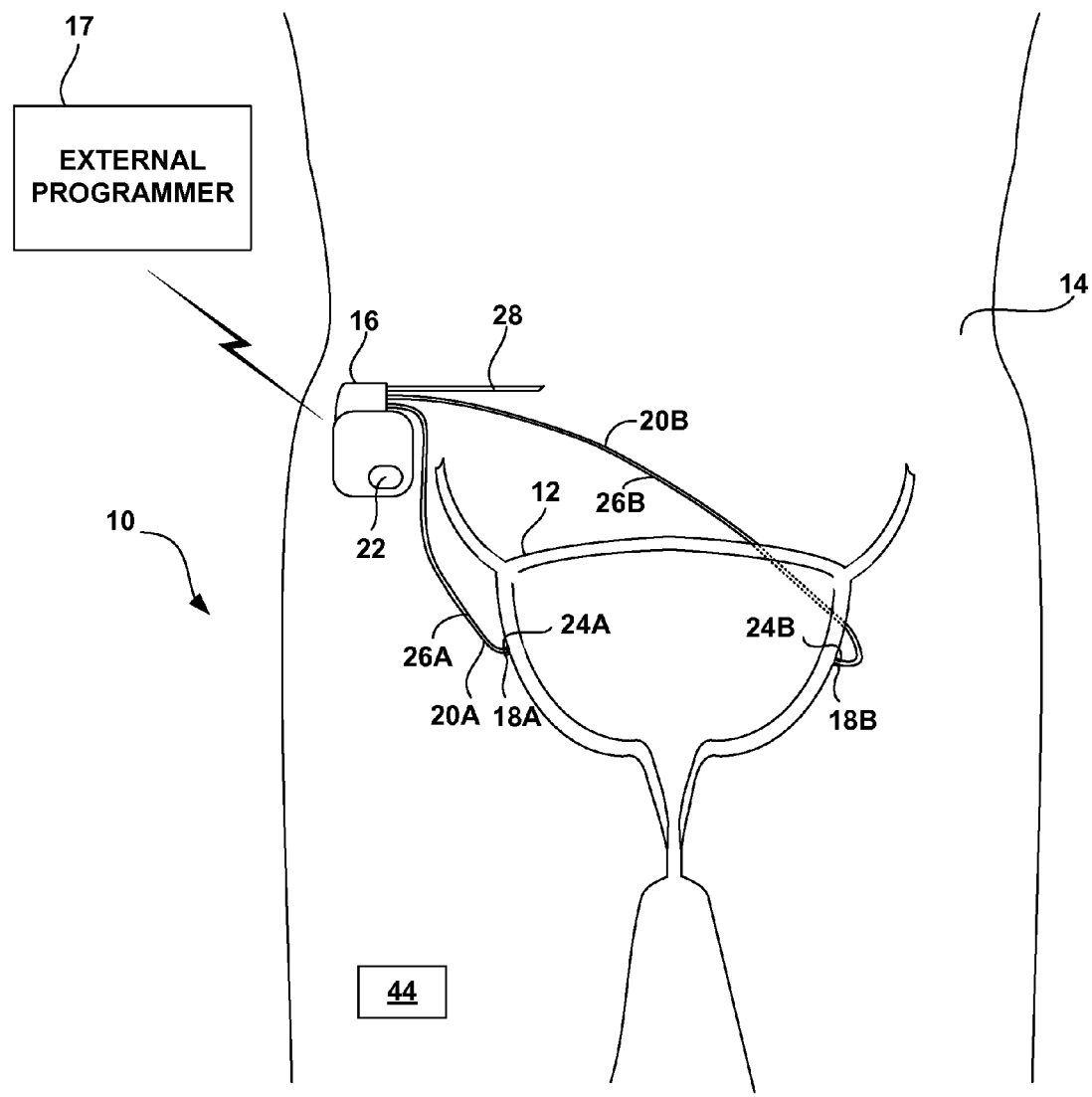
FIG. 1 is a schematic diagram illustrating an example system for determining the filling status of a urinary bladder in accordance with the disclosure.

FIG. 1 is a schematic diagram illustrating an example system 10 that determines the filling status of a urinary bladder 12 of a patient 14 based on electrical impedance of the bladder and the posture of the patient. As shown in FIG. 1, system 10 may include an implantable medical device (IMD) 16 and external programmer 17. System 10 may provide short- or long-term monitoring of bladder functioning or urinary incontinence based on the detected electrical impedance and posture. As such, system 10 may present a patient or caregiver with information related to the filling status of the bladder, or alert the patient if the filling status is above a threshold level, as will be described in more detail below. System 10 may also use the measured bladder impedance and posture as feedback to control delivery of a therapy for alleviating urinary incontinence, such as electrical stimulation therapy, drug therapy, or other incontinence therapy. Other incontinence therapies may include control of valves in mechanical incontinence control devices, for example.

In the illustrated example, IMD 16 is coupled to first and second electrodes 18A and 18B (collectively "electrodes 18") via first and second leads 20A and 20B, respectively (collectively "leads 20"). Electrodes 18 are placed proximate to an exterior surface of the wall of the bladder at first and second locations, respectively. In some examples, electrodes 18 may be sutured or otherwise affixed to the bladder wall. In other examples, electrodes 18 may be implanted into the bladder wall. Electrodes 18 are located at respective locations, and may be located substantially opposite each other relative to the center of bladder 12. For example, electrodes 18A and 18B may be placed on opposite sides of the bladder, either anterior and posterior or left and right.

IMD 16 may transmit an electrical measurement signal, such as a current, through bladder 12 via leads 20 and electrodes 18. The impedance through bladder 12 varies as a function of the filling status of bladder 12, which in turn may vary based on the posture of the patient. Accordingly, IMD 16 also includes a posture sensor such as an accelerometer 22 to detect the posture of patient 14, e.g., upright, lying face down, lying face up, lying face right, lying face left. In some cases a posture sensor also may indicate intermediate postures such as sitting, standing, or the like.

As will be described in more detail below, IMD 16 measures an impedance through bladder 12 based on the transmitted electrical signal, detects a posture based on one or more signals received from accelerometer 22, and determines a fill level of bladder 12 based on the impedance and the posture. In one example, based on the impedance and posture, IMD 16 may transmit to an external device an indication of the fill level of the patient's bladder, thereby acting as a gauge for the patient. In another example, based on the impedance and posture, IMD 16 may automatically provide or vary stimulation, or provide an indication to the patient that stimulation may be required or should be varied.

Figure 2:
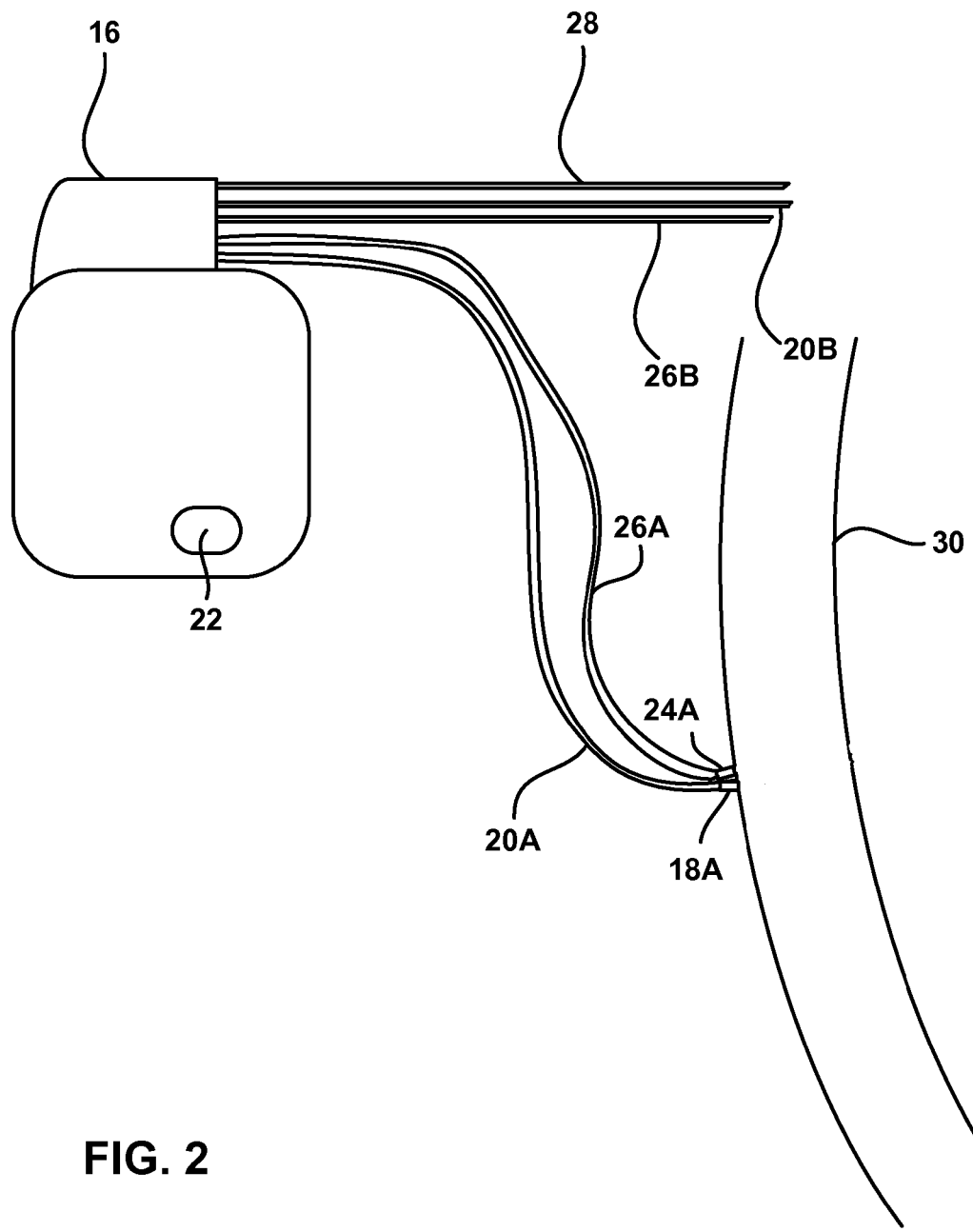
FIG. 2 is an enlarged view of an implantable stimulator with sense and source electrodes proximate a bladder wall in accordance with the disclosure.

While some examples of the disclosure may use a 2-wire measurement technique for measuring the impedance of bladder 12, at least one example may use a 4-wire, or Kelvin, sensing arrangement, as depicted in FIGS. 1 and 2. In addition to being coupled to the first and second electrodes 18 via a first and second leads 20, IMD 16 is coupled to third and fourth electrodes 24A and 24B (collectively "electrodes 24") via third and fourth leads 26A and 26B, respectively (collectively "leads 26"). Alternatively, electrodes 24 may be carried by first and second leads 20 but using different conductors. In an example 4-wire arrangement, IMD 16 sources an electrical signal, such as a current, to electrode 18A via lead 20A, while electrode 18B via lead 20B sinks the electrical signal. IMD 16 then measures the voltage between electrode 24A and electrode 24B via their respective leads, lead 26A and lead 26B. IMD 16 may accurately measure the impedance of the bladder by using a known value of the electrical signal sourced and the measured voltage.

In the example of FIG. 1, IMD 16 is coupled to stimulation lead 28, which may include one or more electrodes as is known in the art for delivering electrical stimulation to patient 14. Stimulation lead 28 may be tunneled from IMD 16 to one or more pelvic floor nerve or muscle sites associated with the urinary system. For example, stimulation lead 28 may terminate adjacent nerves in the pelvic floor, such as the sacral or pudendal nerves which innervates the pelvic floor muscles including the urinary sphincter. For example, sacral or pudendal nerve stimulation may result in an increase in pelvic floor muscle tone or the contraction of the urinary sphincter, which keeps urine inside bladder 12. Appropriate nerve stimulation may assist patient 14 in avoiding urinary incontinence, or promoting the elimination of urine from bladder 12 when urination is desired.

FIG. 2 is an enlarged view of IMD 16 with leads 20 and 26 extending therefrom to dispose electrodes 18A and 24A proximate to the exterior surface of the bladder wall 30 at a first location. Although not illustrated in FIG. 2 for diagrammatic simplicity, electrodes 18B and 24B may be similarly disposed proximate to the exterior surface of the bladder wall 30 at a second location via leads 20B and 26B. IMD 16 is also electrically coupled to stimulation lead 28 which, although not shown in the figures, terminates at a therapy target site. Therapy target sites include pelvic floor muscles and pelvic floor nerves, such as the sacral nerve that innervates the urinary sphincter, the pudendal nerve and its branches, as well as the dorsal genital nerve. Stimulating the sacral nerve may, for example, cause the sphincter to contract and help patient 14 avoid urinary incontinence events. While both leads 20, 26 and stimulation lead 28 carry electrical current, the electrical signals are different from each other and are generated for different purposes. In particular, while leads 20, 26 carry electrical signals for determining the electrical impedance of a patient's bladder, stimulation lead 28 carries electrical signals for treating incontinence, e.g., when applied to the sacral or pudendal nerves. The electrical signal carried by lead 20A is emitted onto or into bladder wall 30 by electrode 18A, and received by electrode 18B on the opposite side of the wall of bladder 12. In some examples, the electrical signal used to determine the electrical impedance of a patient's bladder may be an alternating current with a frequency in the range of approximately 100 hertz (Hz) to approximately 20 kilohertz (kHz). In other examples, the frequency may be in the range of approximately 1 kHz to approximately 10 kHz. In still other examples, the frequency may be in the range of approximately 2 kHz to approximately 6 kHz. In some examples, the electrical signal used to determine the electrical impedance of a patient's bladder may be in the range of about 0.5 microamps to about 100 microamps.

In some examples, electrodes 18, 24 are disposed proximate to the exterior wall of bladder 12, outside of the bladder cavity. While in some examples electrodes 18, 24 may be placed in the interior of the bladder, placing electrodes 18, 24 proximate to the exterior wall eliminates the need to plug or seal holes in the bladder wall in order to contain urine within the bladder. Electrodes 18, 24 may be secured to bladder wall 30 in a manner known to those of ordinary skill, e.g., by sutures, in order to prevent the movement of leads 20, 26 as bladder wall 30 expands and contracts with filling and voiding cycles of bladder 12. In addition, leads 20, 26 may include a flexible material to allow leads 20, 26 to move with the changing size of bladder 12. An inflexible or taught lead 20, 26 could damage the lead, IMD 16, or patient 14. As described above, the techniques described in the disclosure are not limited to examples in which electrodes 18, 24 are located outside bladder 12. In some examples, electrodes 18, 24 may be attached to the inside of bladder wall 30 and thus may be located within the bladder cavity. In one example, electrodes 18, 24 may be embedded within the wall of the bladder.

Leads 20, 26 may include fixation elements, such as barbs, hooks, an expandable, stent-like element, or an expandable hydrogel element to maintain electrodes 18, 24 in desired positions, and prevent the electrodes from separating from bladder wall 30. In examples where the electrodes are located within the bladder cavity, an expandable, stent-like or hydrogel element, or a biological glue, may plug the hole formed by insertion of electrodes and leads through the bladder wall. Such elements or glues may be located inside or outside of bladder when electrodes are positioned within bladder. Leads and electrodes may be advanced into bladder 12 via a hollow, rigid catheter, needle, or the like, which penetrates bladder wall 30, and expansion of a stent-like or hydrogel element may occur after the catheter or needle is withdrawn. Leads may be formed to include a helical section that provides "slack" to allow leads to move with the changing size of bladder.

IMD 16 may be located near bladder 12 or the sacral nerve, for example. Shorter leads 20, 26 may reduce the risk of patient infection, tissue disturbance, and signal noise. In other examples, IMD 16 may wirelessly communicate with a separate implantable stimulation device located near the sacral nerve and an implanted sensor module that detects the impedance through bladder 12. In such examples, IMD 16 may be located in any convenient location that facilitates wireless communication, and need not be coupled to leads 20, 26.

Figure 3:
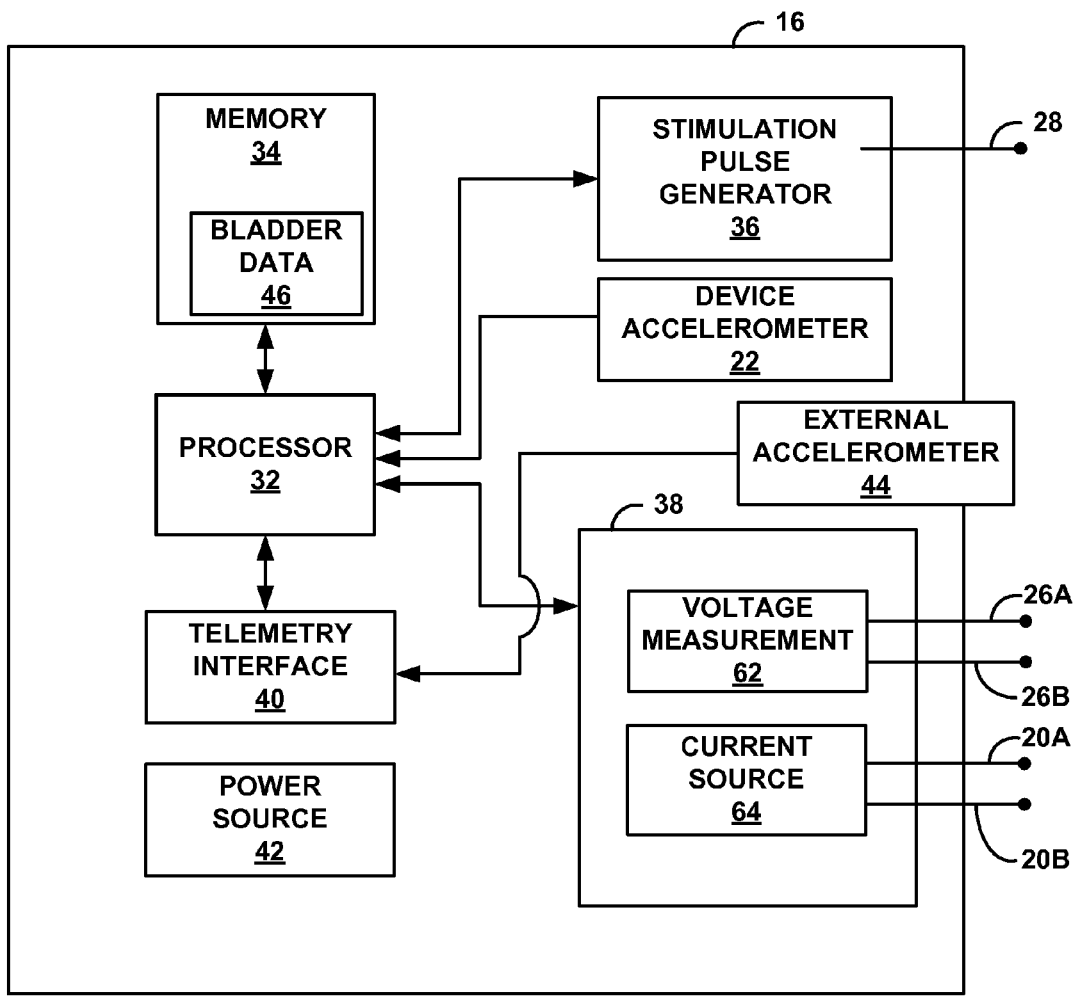
FIG. 3 is a functional block diagram illustrating various components of an implantable medical device which delivers therapy based on a bladder impedance and patient posture in accordance with the disclosure.

FIG. 3 is a functional block diagram illustrating various components of IMD 16. In FIG. 3, IMD 16 includes processor 32, memory 34, stimulation pulse generator 36, impedance measurement circuitry 38, device accelerometer 22, telemetry interface 40, and power source 42. IMD 16 may further be in communication with external accelerometer 44.

IMD 16 may be surgically implanted at a site in patient 14 near the pelvis. The implantation site may be a subcutaneous location in the side of the lower abdomen or the side of the lower back or upper buttocks. One or more electrical stimulation leads 28 may be connected to IMD 16 and surgically or percutaneously tunneled to place one or more electrodes carried by a distal end of the lead at a desired pelvic nerve or muscle site, such as a sacral or pudendal nerve site. IMD 16 has a biocompatible housing, which may be formed from titanium, stainless steel, or the like. IMD 16 may be configured to deliver electrical stimulation pulses with a range of electrical parameter values, such as amplitude, pulse width, and pulse rate selected to prevent involuntary leakage of urine from bladder 12.

In accordance with this disclosure, device accelerometer 22 may be used as a posture sensor to determine the posture of the patient. Device accelerometer 22 may be located within or coupled to the housing of IMD 16 such that device accelerometer 22 detects the motion or relative orientation of IMD 16. Device accelerometer 22 outputs a signal to the processor 32. The relative orientation of device accelerometer 22, indicative of the posture of the patient, is based on the signal generated by device accelerometer 22. In some examples, device accelerometer 22 is a multi-axis accelerometer. However, in at least one example, device accelerometer 22 may be a single-axis accelerometer capable of detecting motion along one axis.

In addition to a first accelerometer, e.g., device accelerometer 22, at least one example of the disclosure provides an accelerometer external to IMD 16 and in communication with the processor 32 of IMD 16, as seen in FIGS. 1 and 3. In one example, a second accelerometer, e.g., external accelerometer 44, may be worn by the patient, such as an accelerometer secured to the patient's thigh, for example, via an elastic band or any other securement means. In such a manner, the combination of the external sensor on the patient's thigh and the device accelerometer may be able to discriminate a sitting position from a standing position. In some examples, external accelerometer 44 may be surgically implanted within the patient, such as within the patient's thigh. Like device accelerometer 22, external accelerometer 44 outputs a signal to processor 32. The relative orientation of external accelerometer 44, indicative of the posture of the patient, is based on the signal.

In some examples, each accelerometer used by system 10 may be an external accelerometer. For example, a single external accelerometer 44 may be used instead of device accelerometer 22. Or, two or more external accelerometers may be used, e.g., a first external accelerometer secured to the patient's thigh and a second external accelerometer secured to the patient's torso. External accelerometer 44 may perform all of the functionality attributed herein to device accelerometer 22.

Processor 32 may compare the signals from the accelerometers, e.g., calculate the difference between the signals received from device accelerometer 22 and external accelerometer 44, to determine the relative movement or orientation of IMD 16 and external accelerometer 44. The relative orientation of device accelerometer 22 and external accelerometer 44 is indicative of the posture of the patient. For multi-axis accelerometers, calculating the difference may involve calculating the difference between each of the axial signals (X, Y, and Z) generated by each of the accelerometers. This calculation may be performed substantially in real-time. Multi-location posture sensing is discussed in detail in U.S. Patent Application Publication No. 2008/0281381.

The processors described in this disclosure may be one or more digital signal processors (DSPs), general purpose microprocessors, application specific integrated circuits (ASICs), field programmable logic arrays (FPGAs), or other equivalent integrated or discrete logic circuitry, or combinations thereof.

Memory 34 may store instructions for execution by processor 32, stimulation therapy data, such as stimulation parameter sets and thresholds, functions or tables used to control therapy delivery based on measured impedance and determined posture, information describing the electrical signal to be transmitted via stimulation lead 28, and information related to bladder impedance data, posture data, and filling status data. Information related to measured impedance and determined posture may be recorded for long-term storage and retrieval by a user, or used by processor 32 for adjustment of stimulation parameters, such as amplitude, pulse width, and pulse rate. Memory 34 may include separate memories for storing instructions, electrical signal information, stimulation therapy data, and bladder data.

Figure 4:
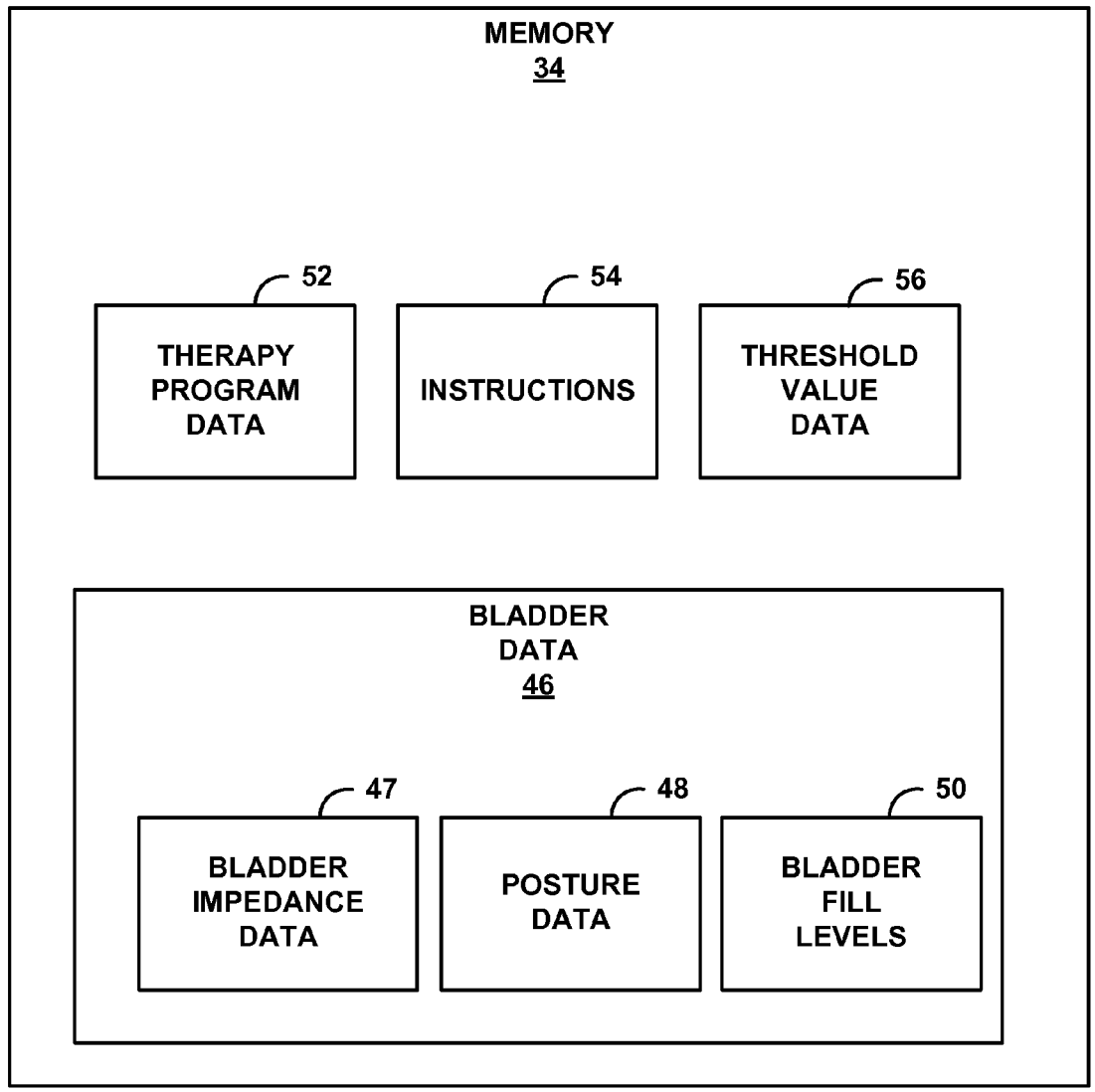
FIG. 4 is a block diagram illustrating storage areas of a memory device in accordance with the disclosure.

As mentioned above, memory 34 may store bladder impedance data and posture data associated with filling status data (collectively "bladder data"), as shown in more detail in FIG. 4. FIG. 4 depicts memory 34 of IMD 16 including bladder impedance data 47, posture data 48, bladder fill levels 50, therapy program data 52, instructions 54 for execution by processor 32, and threshold value data 56 that indicate a level at which either the patient or a caregiver should be alerted as to the filling status of the bladder or therapy should be started or modified. Bladder impedance may vary as a function of the volume of the fluid in the bladder and the posture of the patient. For example, the impedance of a half-full bladder may vary depending on whether the patient is seated or lying down. In one example, the filling status is associated with the impedance and the posture during a programming session. During a programming session, patient 14 may take on a variety of postures, and the impedance through the bladder may be measured for a given volume of fluid in the bladder in each posture. For example, during a programming session a clinician may induce one or more fill stages in patient 14 in a controllable manner by introducing known amounts of fluid into the bladder via a catheter. Posture data may be recorded based on the relative orientation of device accelerometer 22 and optional external accelerometer 44. A clinician may program into memory 34 the impedance data and the posture data associated with the filling status. In particular, memory 34 may store a table that correlates fill levels with impedance values and postures. As an illustration, an impedance value of 2.5 ohms and a posture of lying down may correlate with a particular fill level. The fill level may be expressed, for example, as a level in milliliters (mL) or other volumetric units, or as one of several general fill level categories, such as empty, one-quarter full, one-half full, three-quarter full, and full. In one example, the clinician may first program memory 60 of external programmer 17, shown in FIG. 5, and then download the programs to memory 34 in IMD 16.

By way of example, through a urodynamic study, or by some other method, it may be predetermined by the clinician that a particular patient's bladder may be half-full if it contains 25 mL of fluid. A volume of 25 mL of fluid may result in an impedance through that patient's bladder of 2 ohms when patient is lying on their back. But, a volume of 25 mL of fluid may result in an impedance through the patient's bladder of 2.5 ohms when the same patient is seated upright. The clinician may continue to position the patient in various postures to measure bladder impedance. In memory 34, the clinician may store information that relates the volume of fluid to both the posture of the patient and the bladder impedance. IMD 16, and in particular processor 34, may later access the stored impedance and posture information in memory 34 and determine the filling status of the bladder of the patient. It should be noted that impedance measurement circuitry 38 may detect both the real and reactive components of the electrical impedance of the patient's bladder.

Continuing the example from above, if impedance measurement circuitry 38 measures a bladder impedance of 2 ohms and device accelerometer 22 detects that the patient is lying on his back, processor 32 retrieves from memory 34 the filling status of the bladder, in this case half-full. IMD 16, and in particular memory 34, may store a pre-determined threshold filling status level above which it is necessary to either notify the patient of the filling status, or apply or modify electrical stimulation. If a half-full bladder is below the threshold level, the patient will not be notified and electrical stimulation will not be applied or modified. Using the example from above, if the patient moves from a lying down position to an upright position, the impedance may increase from 2 ohms to 2.5 ohms. Without correlating the impedance and the posture, processor 32 may determine that 2.5 ohms corresponds to a filling status that is above the threshold level. However, in accordance with the techniques of this disclosure, processor 38 retrieves from memory 34 the filling status of the bladder based on an impedance of 2.5 ohms and a seated upright posture. Based on the programming performed by the clinician, the filling status may indicate that the bladder is still half-full. Like before, if a half-full bladder is below the threshold level, the patient will not be notified and electrical stimulation will not be applied. In this manner, IMD 16 may act as a gauge for the patient by providing a true measurement of the filling status of the patient's bladder, regardless of posture.

In at least one example, the filling status is associated with the impedance and the posture using a model, rather than being patient-specific. That is, given certain characteristics of a patient, such as sex, height and weight, the impedance of the patient's bladder and the posture may be based on the analysis provided by the basic body model. Thus, in some examples, the filling status may be determined using a model, while in other examples, the filling status may be determined via measurements of the patient in a clinic.

Processor 32 controls stimulation pulse generator 36 to deliver electrical stimulation therapy via one or more leads 28. Stimulation pulse generator 36 may include voltage or current sources known in the art for generating stimulation. An exemplary range of neurostimulation stimulation pulse parameters likely to be effective in treating incontinence, e.g., when applied to the sacral or pudendal nerves, are as follows:

1. Frequency: between approximately 0.5 Hz and 500 Hz, more preferably between approximately 5 Hz and 250 Hz, and still more preferably between approximately 10 Hz and 50 Hz.

2. Amplitude: between approximately 0.1 volts and 50 volts, more preferably between approximately 0.5 volts and 20 volts, and still more preferably between approximately 1 volt and 10 volts.

3. Pulse Width: between about 10 microseconds and 5000 microseconds, more preferably between approximately 100 microseconds and 1000 microseconds, and still more preferably between approximately 180 microseconds and 450 microseconds.

Processor 32 also controls impedance measurement circuitry 38 to transmit an electrical signal through bladder via leads 20, 26 and electrodes 18, 24. Processor 32 requests impedance measurement circuitry 38 to transmit an electrical signal whenever a bladder measurement is desired. Impedance measurement circuitry 38 may include a voltage measurement circuitry 62 and current source 64, and may include an oscillator (not shown) or the like for producing an alternating signal, as is known in the art. In some examples, as described above with respect to FIG. 1, the impedance measurement circuitry 38 may use a 4-wire, or Kelvin, arrangement. In a 4-wire impedance measurement, the impedance measurement circuitry 38 includes a current source unit 64 and a voltage measurement unit 62, as shown in FIG. 3. The impedance measurement circuitry 38 may include processing circuitry for determining the impedance based on known currents and measured voltages. Impedance measurement circuitry 38 may also include resistors, capacitors, and other known circuits and components for measuring the current and/or voltage of the signal.

Processor 32 may analyze the measured impedance and detected posture, and determine whether any therapy parameter adjustments should be made. For example, processor 32 may compare the bladder impedance and posture combination to one or more thresholds, and then take action to adjust stimulation parameters based on the comparison. Processors 32, 66 may include any one or more of a microprocessor, ASIC, DSP, or other digital logic circuitry. In some examples, the processing circuitry of impedance measurement circuitry 38 that determines an impedance based on a measured voltage and/or current of a signal may be the same microprocessor, ASIC, DSP, or other digital logic circuitry that forms at least part of processors 32, 66.

Stimulation pulse generator 36 provides electrical stimulation according to the stored parameter values via one or more leads 28 implanted proximate to a pelvic nerve, such as a sacral or pudendal nerve, or muscle. Processor 32 determines any parameter adjustments based on the measured impedance and detected posture, and loads the adjustments into memory 34 for use in delivery of stimulation.

The thresholds stored in memory 34 and used to control delivery of therapy based on bladder impedance and patient posture may be determined based on calibration. In some examples, the thresholds may be determined during implantation of IMD 16. For example, during implantation, a surgeon may empty the bladder to identify a lower limit threshold impedance value associated with low bladder volume, and fill the bladder to identify an upper limit impedance value associated with high bladder volume. Such lower and upper limits may be associated with low intensity and high intensity stimulation levels, used to interpolate intermediate thresholds and stimulation levels. Further, such thresholds may be identified or adapted over time based on user input, e.g., via external programmer 17, which may indicate whether the bladder has been emptied or feels full, or an incontinence event has occurred. Processor 32, or a processor of another computing device, such as external programmer 17, may determine the thresholds during calibration.

Also, therapy parameters may be automatically adjusted based on the analysis provided by the basic body model. In other examples, the analysis provided by the basic body model may complement a programming session or learning mode. For example, during a programming session, the basic body model may provide a starting point or suggestion of how to adjust the therapy parameters based on impedance and posture. The clinician or patient may accept the therapy suggested by the basic body model and/or fine tune the therapy to better treat the symptoms of patient 14. Likewise, during a learning mode, the therapy suggested by the basic body model may be implemented (e.g., automatically or manually) and/or fine tuned by patient 14.

During the programming session, therapy parameters may also be optimized in each posture and stored in memory 34. In some examples that include a device accelerometer 22 and no external accelerometer 44, memory 34 may store the relative orientation of accelerometer 22, as well as the programmed therapy parameters, e.g., therapy programs, specific to each posture in association with an indication of the relative orientation. In other examples that include both a device accelerometer 22 and external accelerometer 44, memory 34 may store the relative orientation of accelerometers 22, 44, as well as the programmed therapy parameters, e.g., therapy programs, specific to each posture in association with an indication of the relative orientation. After such a programming session, IMD 16 may adjust the therapy delivered to patient 14 based on the posture of patient 14 by, for example, periodically determining the impedance of the bladder and identifying the relative orientation of accelerometers 22, 44 based on the signals generated by the accelerometers, and selecting a program associated with the impedance and the relative orientation.

Techniques for interpreting the detected impedance and determining therapy parameter adjustments based thereon are described in detail in U.S. Patent Application Publication No. 2007/0100387.

Telemetry interface 40 may include circuitry to support telemetry communication by radio frequency (RF) communication or proximal induction, as is known in the art. As mentioned above, external accelerometer 44 outputs a signal to processor 32. The relative orientation of external accelerometer 44, indicative of the posture of the patient, is based on the signal. In one example, external accelerometer 44, either worn by or implanted in the patient, includes wireless circuitry enabling it to output a wireless signal to processor 32 via the telemetry interface 40. In such a manner, processor 32 may compare the signals from device accelerometer 22 and external accelerometer 44 to determine the relative orientation of device accelerometer 22 and external accelerometer 44. The relative orientation of device accelerometer 22 and external accelerometer 44 is indicative of the posture of the patient. In other examples that include only a multi-axis device accelerometer 22 and no external accelerometer 44, processor 32 may analyze the output of device accelerometer 22 in order to determine the posture of the patient.

Power source 42 of IMD 16 delivers operating power to the components of IMD 16. Power source 42 may be a rechargeable or non-rechargeable battery, or alternatively take the form of a transcutaneous inductive power interface.

Figure 5:
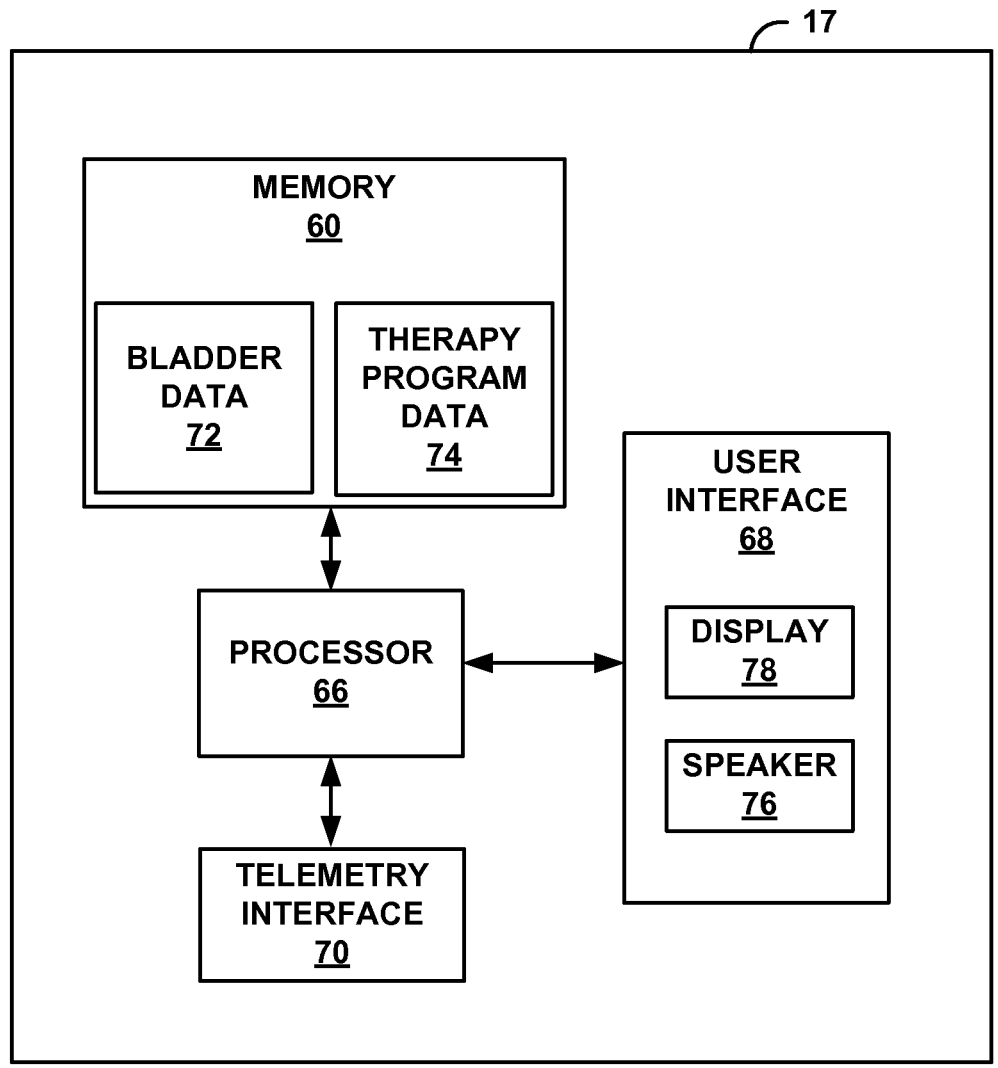
FIG. 5 is a functional block diagram illustrating various components of an example external programmer in accordance with the disclosure.

FIG. 5 is a functional block diagram illustrating various components of an example external programmer 17. As illustrated in FIG. 5, external programmer 17 may include a processor 66, memory 60, user interface 68, and telemetry interface 70. Memory 60 may store program instructions that, when executed by processor 66, cause processor 66 and external programmer 17 to provide the functionality ascribed to external programmer 17 throughout this disclosure. Memory 60 may further include therapy program data 72 and bladder data 74, as shown in FIG. 5, which may be downloaded into memory 34 of IMD 16. In one example, bladder data 46 of IMD 16 is identical to bladder data 72 of external programmer 17, and therapy program data 52 of IMD 16 is identical to therapy program data 74 of external programmer 17.

User interface 68 may include a button or keypad, lights, speaker 76, and display 78, such as a liquid crystal (LCD), light-emitting diode (LED), or cathode ray tube (CRT) display. As discussed in this disclosure, processor 66 may present information relating to measured impedance, determined posture, as well as bladder parameters such as volume, or bladder filling and emptying via the user interface 68. Processor 66 may provide alerts related to bladder volume to patient 14 or a caregiver, as will be described in more detail below, via user interface 68. Although not shown, external programmer 17 may additionally or alternatively include a data or network interface to another computing device, to facilitate communication with the other device, and presentation of information relating to measured impedance, detected posture, bladder parameters such as volume, or bladder filling, and emptying via the other device.

Further, processor 66 may receive information related to measured impedance and detected posture from IMD 16 via telemetry interface 70, and adjust therapy based on the detected impedance through communication with IMD 16 via the telemetry interface. Telemetry interface 70 may be substantially similar to telemetry interface 40 described above, providing wireless communication via an RF or proximal inductive medium. Patient 14 may indicate an intent to void, and processor 66 may effect a blanking interval for the detected impedance, either within external programmer 17, or through communication of the indication to IMD 16 via telemetry interface 70. Processor 66 may also request impedance detection through communication with IMD 16 via the telemetry interface.

External programmer 17 may be a small, battery-powered, portable device that accompanies patient 14 throughout a daily routine. Programmer 17 may have a simple user interface, such as a button or keypad, and a display or lights. Patient 14 may voluntarily initiate a voiding event, i.e., a voluntary voiding of bladder 12, via the user interface. In this case, programmer 17 may transmit a command signal to IMD 16 to temporarily suspend stimulation, and thereby permit voluntary voiding. In some examples, the length of time for a voiding event may be determined by pressing and holding down a button for the duration of a voiding event, pressing a button a first time to initiate voiding and a second time when voiding is complete, or by a predetermined length of time permitted by programmer 17 or IMD 16. In each case, programmer 17 causes implantable IMD 16 to temporarily suspend stimulation so that voluntary voiding is possible. However, in other examples, suspension of stimulation is not necessary to facilitate voiding, and stimulation may occur substantially continuously, with modifications based on the detected impedance.

It should be noted that control of the electrical stimulation may come from within IMD 16 or from an external programmer such as external programmer 17, or from a combination of the two. If external programmer 17 controls the electrical stimulation, the external programmer may transmit to IMD 16 via telemetry interface 70 program commands for adjusting the therapy programs, e.g., therapy programs, based on the patient's posture. Or, external programmer may transmit a signal to IMD 16, indicating that IMD 16 should execute locally stored program based on the patient's posture. In such a manner, control over the electrical stimulation may be distributed between IMD 16 and an external programmer, or may reside in either one alone.

In one example, techniques of this disclosure may present a patient with information related to the filling status of their bladder via user interface 68. That is, after measuring the impedance of the bladder and determining the posture of a patient, processor 32 of IMD 16 may select a filling status of the bladder from memory 34 based on these parameters and communicate the status to the patient via user interface 68 of external programmer 17. For example, user interface 68 may provide a visual signal to the patient via its display 78. A visual signal may be a color-coded graphic indicating the filling status of the bladder, where the color red may indicate a full bladder. Or, in another example, if processor 32 determines that the filling status of the patient's bladder is above a threshold level, user interface 68 may provide an audible signal to the patient via its speaker 76. In response, the patient may use programmer 17 to initiate a therapy intended to promote urination. Or, the patient may terminate a therapy intended to promote urinary retention if, for example, a voiding event has occurred. Alerting the patient when the bladder volume reaches a threshold may allow a patient to avoid an incontinence event, or reduce pelvic pain in cases where the patient has a condition such that a relatively full bladder causes pelvic pain, as with interstitial cystitis. In some examples, therapy may be delivered substantially continuously, but at different intensities based on the detected impedance.

In at least one example, IMD 16 may adaptively learn a patient's voiding routine. For example, the patient may use external programmer 17 to indicate a full bladder sensation. In other words, the patient may use user interface 68 of external programmer 17 to input a full level. In response, processor 32 of IMD 16 instructs impedance measurement circuitry 38 of IMD 16 to measure the impedance and determine the posture of the patient, and then writes the impedance measurement and posture information to memory 34. Then, after a voiding event, the patient may use user interface 68 of external programmer 17 to input an empty level. In response, processor 32 of IMD 16 instructs impedance measurement circuitry 38 of IMD 16 to measure the impedance and determine the posture of the patient, and then writes the impedance measurement and posture information to memory 34. Later, when the patient's bladder fills to the level at which the patient previously voided, as determined by the impedance measurements and posture detection techniques described above, IMD 16 may alert the patient via user interface 68 of external programmer 17. In such a manner, IMD 16 may adaptively learn a patient's voiding routine.

In another example, the patient may control the therapy delivered by IMD 16 via external programmer 17. For example, the patient may initiate or terminate delivery of therapy by IMD 16 via external programmer 17. Further, IMD 16 or external programmer 17 may control delivery of therapy based on the measured bladder impedance and determined posture by initiating, adjusting, or terminating the therapy. For example, IMD 16 or external programmer 17 may adjust electrical stimulation parameters such as pulse amplitude, rate and width, and electrode polarity or configuration, based on the measured impedance and the determined posture. If the measured impedance and determined posture indicates increased bladder volume, IMD 16 or external programmer 17 may increase the intensity of therapy intended to promote urinary retention. After a voiding event, the IMD 16 or external programmer 17 may terminate or reduce the intensity of the therapy to conserve power or other resources.

Figure 6:
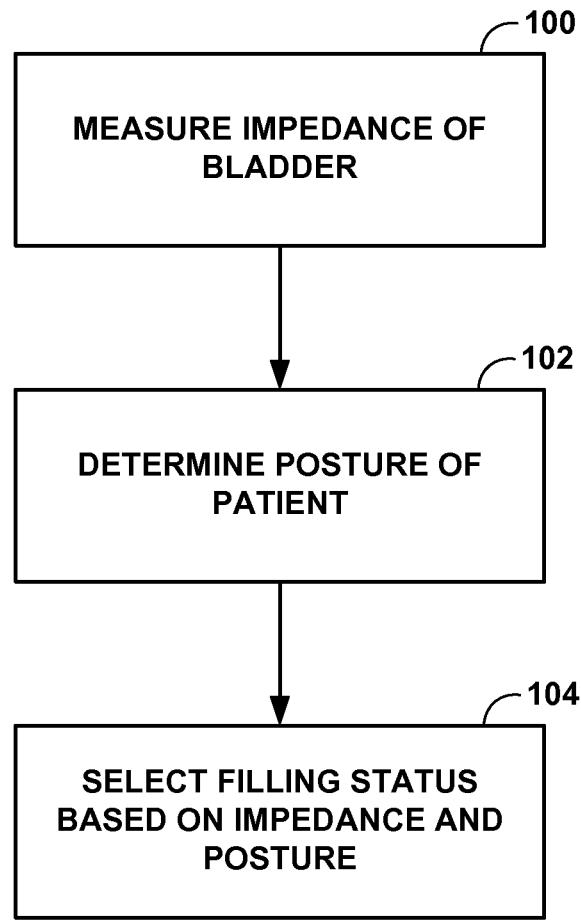
FIG. 6 is a flow chart illustrating an example technique for detecting the filling status of a urinary bladder of a patient based on a bladder impedance and patient posture in accordance with the disclosure.

FIG. 6 is a flow chart illustrating one method for detecting the filling status of a urinary bladder of a patient based on a bladder impedance in accordance with the disclosure. Impedance measurement circuitry 38 measures the impedance of the bladder (100). Device accelerometer 22, and optionally external accelerometer 44, determines the posture of the patient (102). Processor 32 then accesses memory 34 and selects a bladder filling status based on the measured impedance and the determined posture (104). In some examples, processor 32 is the processor in IMD 16. In other examples, processor 32 is the processor in external programmer 17.

Figure 7:
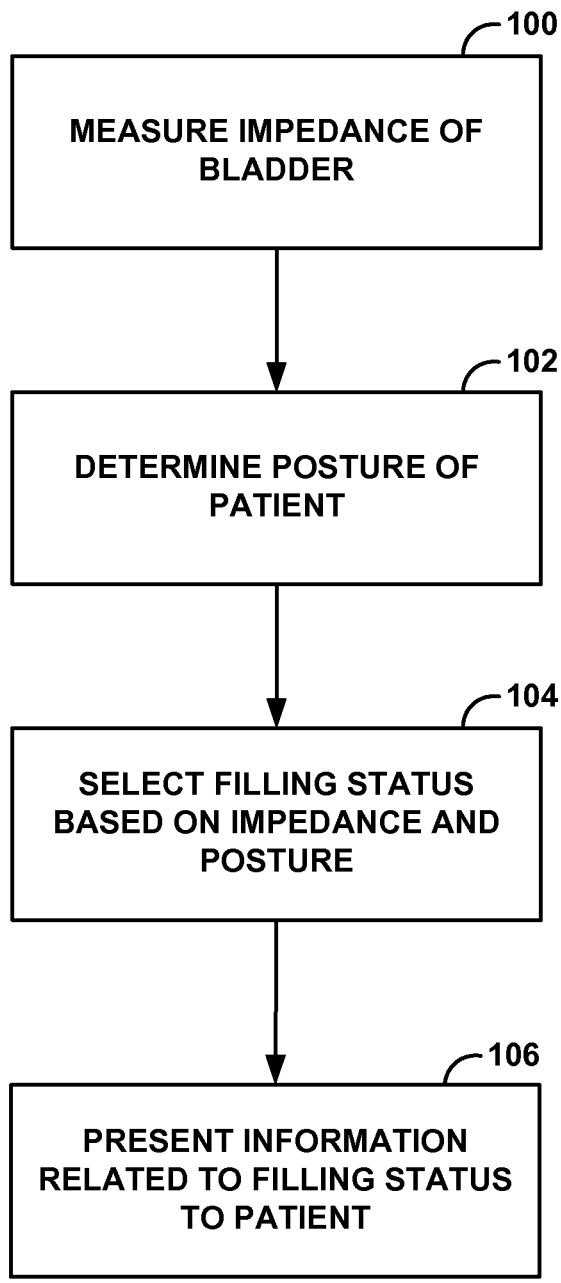
FIG. 7 is a flow chart illustrating another example technique for detecting the filling status of a urinary bladder of a patient based on a bladder impedance and patient posture in accordance with the disclosure.

FIG. 7 is flow chart illustrating another method for detecting the filling status of a urinary bladder of a patient based on a bladder impedance in accordance with the disclosure. The method of FIG. 7 is similar to the method of FIG. 6, and similar steps are indicated by the same reference number. Device accelerometer 22, and optionally external accelerometer 44, determines the posture of the patient (102). Processor 32 then accesses memory 34 and selects a bladder filling status based on the measured impedance and the determined posture (104). In FIG. 7, after the filling status is selected by processor 32 (104), external programmer 17 presents information related to the filling status to the patient (106). For example, if the impedance and posture indicate that the bladder is nearly full, the display on the external programmer may turn red, indicating to the patient that it may be desirable to void their bladder.

Figure 8:
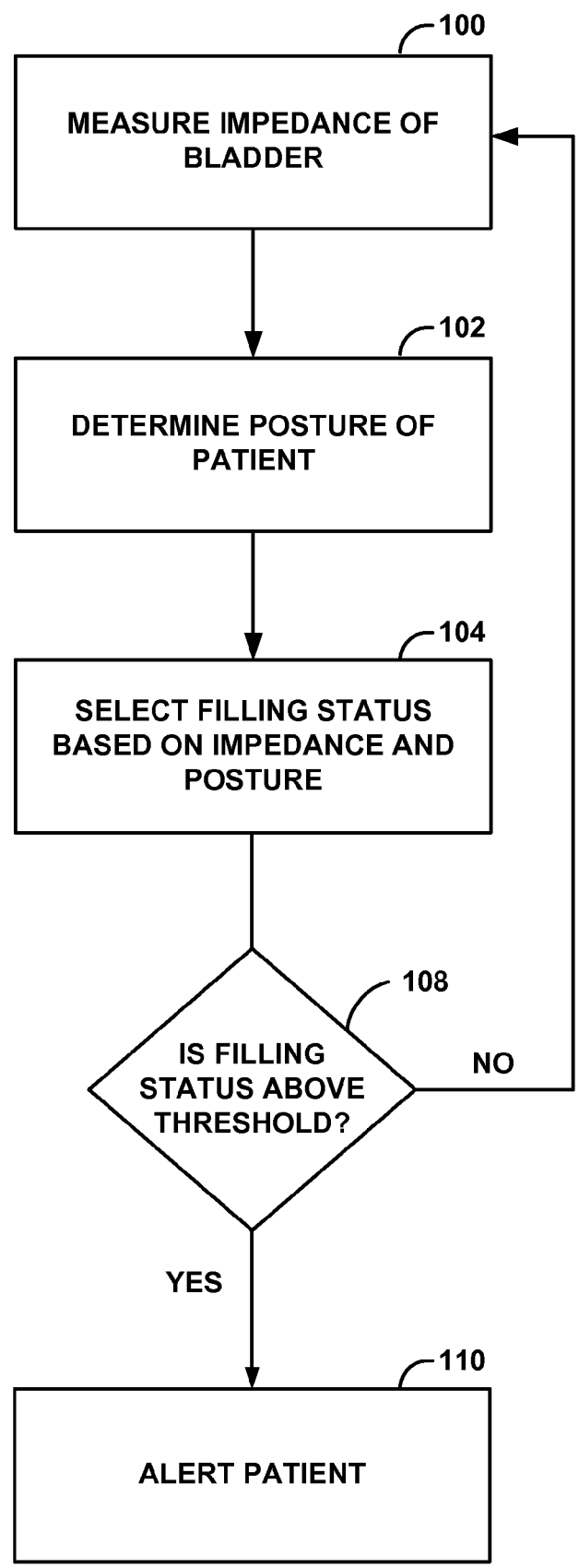
FIG. 8 is a flow chart illustrating another example technique for detecting the filling status of a urinary bladder of a patient based on a bladder impedance and patient posture in accordance with the disclosure.

FIG. 8 is flow chart illustrating yet another method for detecting the filling status of a urinary bladder of a patient based on a bladder impedance in accordance with the disclosure. The method of FIG. 8 is similar to the method of FIG. 6, and similar steps are indicated by the same reference number. Device accelerometer 22, and optionally external accelerometer 44, determines the posture of the patient (102). Processor 32 then accesses memory 34 and selects a bladder filling status based on the measured impedance and the determined posture (104). In FIG. 8, after the filling status is selected by processor 32 (104), processor 32 compares the filling status selected to threshold value data 56 stored in memory 34 and determines whether the filling status is above the threshold level (108). If the filling status is above the threshold level, then processor 32 provides a signal to speaker 76, display 78, or otherwise alerts patient 14 (110). If the filling status is below the threshold value data 56, IMD 16, and in particular impedance measurement circuitry 38 continues to measure bladder impedance (100).

Figure 9:
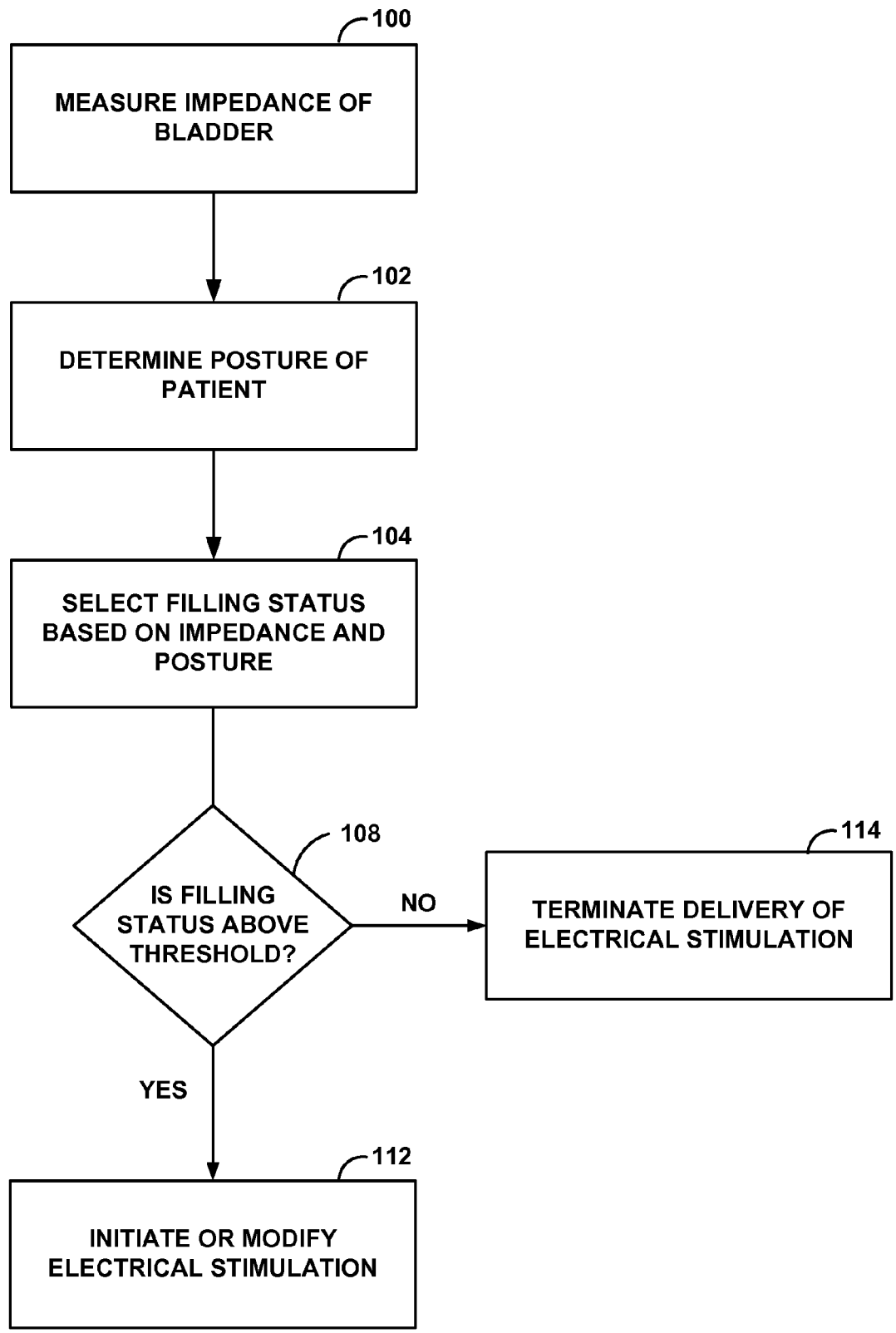
FIG. 9 is a flow chart illustrating another example technique for detecting the filling status of a urinary bladder of a patient based on a bladder impedance and patient posture in accordance with the disclosure.

FIG. 9 is flow chart illustrating yet another method for detecting the filling status of a urinary bladder of a patient based on a bladder impedance in accordance with the disclosure. The method of FIG. 9 is similar to the method of FIG. 8, and similar steps are indicated by the same reference number. Device accelerometer 22, and optionally external accelerometer 44, determines the posture of the patient (102). Processor 32 then accesses memory 34 and selects a bladder filling status based on the measured impedance and the determined posture (104). In FIG. 9, after the filling status is selected by processor 32 (104), processor 32 compares the filling status selected to threshold value data 56 stored in memory 34 and determines whether the filling status is above the threshold level (108). If the filling status is above the threshold level, then processor 32 instructs stimulation pulse generator 36 to initiate or modify delivery of electrical therapy via stimulation lead 28 to the patent (112). If the filling status is below the threshold value data 56, then processor 32 may instruct stimulation pulse generator 36 to terminate delivery of electrical therapy (114).

The techniques described in this disclosure may provide certain advantages. In some aspects, the techniques of the disclosure may allow patients suffering from spinal injuries, who often lack the normal sensation of a full bladder, to know when their bladder should be voided. In other aspects, the techniques of this disclosure may allow a patient to know the true filling status of their bladder. In another aspect, the techniques of this disclosure may allow a patient to vary stimulation parameters based on the true filling status of their bladder.

The techniques described in this disclosure may be implemented in hardware, software, firmware, or any combination thereof. In particular, the techniques may be implemented in a hardware device, such as a wireless communication device or network device, either of which may include software and/or firmware to support the implementation. For portions implemented in software, the techniques may be realized in part by a computer-readable medium comprising program code containing instructions that, when executed, performs one or more of the methods described above. In this case, the computer readable medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like.

The program code may be executed by one or more processors, such as one or more digital signal processors (DSPs), general purpose microprocessors, an application specific integrated circuits (ASICs), field programmable logic arrays (FPGAs), or other equivalent integrated or discrete logic circuitry. In this sense, the techniques are implemented in hardware, whether implemented entirely in hardware or in hardware such as a processor executing computer-readable code.

The code may be executed by one or more processors, such as one or more digital signal processors (DSPs), general purpose microprocessors, an application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein.

The invention claimed is:

1. A method comprising:
  receiving, by a processor in a medical device system, a measured impedance value of a urinary bladder of a patient;
  receiving, by the processor, a determined posture of the patient; and
  determining, with the processor, a filling status of the urinary bladder of the patient based on the measured impedance value of the bladder of the patient and the determined posture of the patient, wherein the measured impedance value is associated with a plurality of filling statuses, the plurality of filling statuses including the determined filling status.

2. The method of claim 1, further comprising:
  measuring the impedance value of the bladder of the patient with an implanted medical device; and wherein receiving a determined posture of the patient comprises:
    sensing a signal indicative of a posture of the patient with a posture sensor; and
    determining, with the processor, the posture of the patient based on the sensed signal.

3. The method of claim 2, wherein the posture sensor comprises one or more accelerometers, and wherein determining the posture comprises determining the posture based on one or more signals from the one or more accelerometers.

4. The method of claim 2, wherein measuring the impedance value of the bladder of the patient comprises:
  emitting an electrical signal via a first electrode implanted proximate to a wall of the bladder at a first location,
  receiving the electrical signal via a second electrode implanted proximate to the wall of the bladder at a second location, and
  measuring the impedance value of the bladder based on the electrical signal.

5. The method of claim 4, wherein measuring the impedance value of the bladder of the patient further comprises:
  measuring a voltage between a third electrode implanted adjacent to the first electrode and a fourth electrode implanted adjacent to the second electrode; and
  measuring the impedance value of the bladder based on the electrical signal and the measured voltage.

6. The method of claim 1, wherein the filling status comprises at least one of a volumetric indication of an amount of urine in the bladder or a fill level category.

7. The method of claim 1, wherein determining the filling status of the bladder comprises determining the filling status from a plurality of filling statuses, wherein the filling status is associated with the measured impedance value and the determined posture.

8. The method of claim 1, further comprising generating an alert if the determined filling status indicates a fill level of the bladder above a threshold level.

9. The method of claim 1, further comprising controlling an implanted medical device to deliver therapy to the patient based on the determined filling status.

10. The method of claim 9, wherein the therapy comprises electrical stimulation therapy delivered to at least one of a pelvic floor nerve or a pelvic floor muscle based on the determined filling status.

11. The method of claim 7, wherein each of the plurality of filling statuses is associated with a respective impedance value of the bladder and a respective posture of the patient in a memory, and wherein determining the filling status from the plurality of filling statuses comprises determining the filling status associated with the measured impedance value and the determined posture in the memory.

12. A system comprising:
  an implantable medical device comprising an impedance measurement unit configured to measure an impedance value of a urinary bladder of a patient;
  a posture sensor configured to sense a signal indicative of a posture of the patient; and a processor configured to determine the posture of the patient based on the sensed signal and determine a filling status of the bladder based on the measured impedance value and the determined posture, wherein the measured impedance value is associated with a plurality of filling statuses, the plurality of filling statuses including the determined filling status.

13. The system of claim 12, wherein the posture sensor comprises one or more accelerometers, and wherein the processor is configured to determine the posture of the patient based on one or more signals from the one or more accelerometers.

14. The system of claim 12, further comprising:
a first electrode implantable proximate to a wall of a bladder of a patient at a first location; and
a second electrode implantable proximate to the wall of the bladder at a second location,
wherein the impedance measurement unit is electrically coupled to the first electrode and the second electrode, and wherein the impedance measurement unit is configured to emit an electrical signal via the first electrode, receive the electrical signal via the second electrode, and measure an impedance value of the bladder based on the electrical signal.

15. The system of claim 14, further comprising:
a third electrode implantable adjacent to the first electrode and a fourth electrode implantable adjacent to the second electrode,
wherein the impedance measurement unit is configured to measure a voltage between the third and fourth electrodes, and measure the impedance value of the bladder based on the electrical signal and the measured voltage.

16. The system of claim 12, wherein the filling status comprises at least one of a volumetric indication of an amount of urine in the bladder or a fill level category.

17. The system of claim 12, wherein the processor is configured to determine the filling status of the bladder from a plurality of filling statuses, wherein the determined filling status is associated with the measured impedance value and the determined posture.

18. The system of claim 12, wherein the processor is configured to generate an alert if the filling status indicates a fill level above a threshold level.

19. The system of claim 12, wherein the processor is configured to control the implantable medical device to deliver therapy to the patient based on the determined filling status.

20. The system of claim 19, wherein the implantable medical device comprises an electrical stimulation therapy device configured to deliver electrical stimulation to at least one of a pelvic floor nerve or a pelvic floor muscle.

21. The system of claim 17, further comprising a memory, wherein each of the plurality of filling statuses is associated with a respective impedance value of the bladder and a respective posture of the patient in the memory, and wherein the processor is configured to determine the filling status from the plurality of filling statuses based on the measured impedance value and the determined posture in the memory.

22. An implantable medical device comprising:
an impedance measurement unit configured to measure an impedance value of a urinary bladder of a patient;
a posture sensor configured to sense a signal indicative of a posture of the patient; and
a processor configured to determine the posture of the patient based on the sensed signal and determine a filling status of the bladder based on the measured impedance value and the determined posture, wherein the measured impedance value is associated with a plurality of filling statuses, the plurality of filling statuses including the determined filling status.

23. The device of claim 22, wherein the posture sensor comprises one or more accelerometers configured to generate one or more signals indicative of posture, and wherein the processor is configured to determine the posture based on the one or more signals.

24. The device of claim 22, further comprising:
a first electrode implantable proximate to a wall of a bladder of a patient at a first location; and
a second electrode implantable proximate to the wall of the bladder at a second location,
wherein the impedance measurement unit is electrically coupled to the first electrode and the second electrode, and wherein the impedance measurement unit is configured to emit an electrical signal via the first electrode, receive the electrical signal via the second electrode, and measure an impedance value of the bladder based on the electrical signal.

25. The device of claim 24, further comprising:
a third electrode implantable adjacent to the first electrode; and
a fourth electrode implantable adjacent to the second electrode,
wherein the impedance measurement unit is configured to measure a voltage between the third and fourth electrodes and measure the impedance of the bladder based on the electrical signal and the measured voltage.

26. The device of claim 22, wherein the processor is configured to determine the filling status from a plurality of filling statuses, wherein the determined filling status is associated with the measured impedance and the detected posture.

27. The device of claim 22, wherein the processor is configured to generate an alert if the filling status indicates a fill level above a threshold level.

28. The device of claim 22, further comprising a therapy delivery unit, wherein the processor is configured to control the therapy delivery unit to deliver therapy to the patient based on the determined filling status.

29. The device of claim 28, wherein the therapy delivery unit comprises an electrical stimulation therapy unit configured to deliver electrical stimulation to at least one of a pelvic floor nerve or a pelvic floor muscle.

30. An external programmer for an implantable medical device, the programmer comprising:
a telemetry interface configured to receive data indicating a measured impedance value of a bladder of a patient from the implantable medical device; and
a processor configured to determine a posture of the patient and determine a filling status of the bladder of the patient based on the measured impedance value and the determined posture, wherein the measured impedance value is associated with a plurality of filling statuses, the plurality of filling statuses including the determined filling status.

31. The external programmer of claim 30, wherein the telemetry interface is configured to receive posture data indicating the posture of the patient and the processor is configured to determine the posture based on the posture data.

32. The external programmer of claim 30, wherein the filling status comprises at least one of a volumetric indication of an amount of urine in the bladder or a fill level category.

33. The external programmer of claim 30, wherein the processor is configured to determine the filling status from a plurality of filling statuses, wherein the determined filling status is associated with the measured impedance value and the determined posture.

34. The external programmer of claim 30, wherein the processor is configured to at least one of generate an alert if the filling status indicates a fill level above a threshold level or control the implantable medical device to deliver therapy to the patient based on the determined filling status.

\* \* \* \* \*